US00PP24727P3

(12) United States Plant Patent
Olesen

(10) Patent No.: US PP24,727 P3
(45) Date of Patent: Aug. 5, 2014

(54) FLORIBUNDA ROSE PLANT NAMED 'POULNAP001'

(50) Latin Name: ***Rosa* hybrid**
Varietal Denomination: Poulnap001

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 91 days.

(21) Appl. No.: 13/507,020

(22) Filed: May 31, 2012

(65) Prior Publication Data

US 2013/0326763 P1 Dec. 5, 2013

(51) Int. Cl.
*A01H 5/00* (2006.01)

(52) U.S. Cl.
USPC ..... Plt./148; Plt./101; Plt./141

(58) Field of Classification Search
USPC ..... Plt./101, 141, 148
See application file for complete search history.

*Primary Examiner* — Susan McCormick Ewoldt

(57) ABSTRACT

A new garden rose plant of the floribunda class which has abundant, pink flowers and attractive foliage. This new and distinct variety has shown to be uniform and stable in the resulting generations from asexual propagation.

1 Drawing Sheet

Botanical designation: *Rosa* hybrid.
Variety denomination: 'Poulnap001'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2000 and the resulting seeds were planted in a controlled environment in Fredensborg, Denmark. The new variety, named 'Poulnap001', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poulnap001' from all other varieties of which we are aware.

As part of the rose development program, Mogens N. Olesen germinated the seeds from the aforementioned hybridization during winter of 2000 and conducted evaluations on the resulting seedlings in a controlled environment in Fredensborg, Denmark. 'Poulnap001' was selected in the spring of 2001 by the inventor as a single plant from the progeny of the aforementioned hybridization.

Asexual reproduction of 'Poulnap001' by traditional budding and rooted cuttings was first done by Mogens N. Olesen in the nursery in Fredensborg, Denmark in July, 2001. This initial and other subsequent asexual propagations conducted in controlled environments have demonstrated that the characteristics of 'Poulnap001' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulnap001'. Specifically illustrated in the drawing are flowers at various stages of development, flower in parts, leaves, and stems. Illustrated plants are 2 years of age.

DETAILED DESCRIPTION OF THE VARIETY

The following is a description of 'Poulnap001', as observed in its growth in in a field nursery in Marion County, Oreg. Observed plants are 3 years of age, and were grown on their own roots. Color references are made using The Royal Horticultural Society (London, England) Colour Chart, 2001, except where common terms of color are used.

For a comparison, several physical characteristics of the rose variety 'Poulbella', U.S. Plant Pat. No. 12,904 are compared to 'Poulnap001' in Chart 1.

CHART 1

| | 'Poulnap001' | 'Poulbella' |
|---|---|---|
| Petal Count | 50 petals, 10 to 13 of which are petaloids | 35-40 petals |
| Flower Diameter | 60 to 65 mm | 50 to 80 mm |
| General Tonality of Flower Color | Red Group 54C and Red Group 49A | Red-Purple Group 57C |

FLOWER AND FLOWER BUD

Blooming habit: Continuous.

Flower bud:

*Size*.—Upon opening, 28 mm in length from base of receptacle to end of bud. Bud diameter is 13 mm.

*Bud form*.—Ovoid.

*Bud color*.—As sepals divide petals are Red Group 41B.

*Sepal inner surface*.—Color: Green Group 138B. Surface: Smooth, moderately pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—30 mm long by 10 mm wide.

*Receptacle*.—Texture: Smooth. Size: 10 mm in height by 8 mm wide. Color: Yellow-Green Group 144A. Shape: Funnel.

*Pedicel*.—Surface: Smooth. Length: 30 to 35 mm. Diameter: 3 mm on average. Color: Yellow-Green Group 144A with weak anthocyanic pigments the color of Greyed-Orange Group 174A. Strength: Moderate.

*Peduncle*.—Length: 2 cm average. Diameter: 3 mm average. Color: Yellow-Green Group 144A.

Flower bud development: Flower buds are borne in clusters of 1 to 3 flower buds per stem, resembling a corymb.

Flower bloom:

*Fragrance*.—Moderate rose perfume.

*Duration*.—The blooms have a duration on the plant of approximately 10 days. Petals fall cleanly away from plant after flowers have fully matured.

*Size*.—Flower diameter is 60 to 65 mm when open. Flower depth is 35 mm.

*Flower shape*.—General shape is high centered, semi double, with a high pointed center which is tightly closed.

*Shape of flower, side view*.—Upon opening the upper portion is a flattened convex. The lower portion is a flattened convex.

Petalage: Under normal conditions, flowers have 50 petals, 10 to 13 of which are petaloids.

General tonality of flower: Open flowers are Red Group 54C and Red Group 49A.

Petal color:

*Upon opening, outer petals*.—Upper surface: Red Group 49A. Lower surface: Red Group 49A with intonations of Red Group 50B at the margins.

*Upon opening, inner petals*.—Upper surface: Red Group 49A with intonations of Orange Group29B at the basal zone. Lower surface: Red Group 49A. Basal zone is Orange Group 29C.

*Basal petal spots, upon opening*.—Upper surface: Yellow Group 7C. Lower surface: Yellow Group 7C.

*After opening, outer petals*.—Upper surface: Red Group 55C. Lower surface: Red Group 56A.

*After opening, inner petals*.—Upper surface: Red Group 49A with intonations of Red Group 36B. Lower surface: Red Group 56B with intonations of Red Group 36A.

*Basal petal spots, after opening*.—Upper surface: Yellow Group 7C. Lower surface: Yellow Group 7C.

Petals:

*Petal reflex*.—Moderately reflexed.

*Margin*.—Entire and uniform. No undulations of margin observed.

*Shape*.—Generally narrow ecliptic. Apex shape: Rounded. Base shape: Acute.

*Size*.—40 mm (l)×30 mm (w).

*Texture*.—Smooth.

*Thickness*.—Average.

Petaloids:

*Size*.—40 mm (l) by 30 mm (w).

*Quantity*.—25 to 18 mm.

*Shape*.—The apex is rounded with a cleft. The base is acute.

*Color*.—Upper surface is Red Group 40C. The lower surface is Red Group 37A. Spots at the base are Yellow Group 6A.

Reproductive organs:

*Pollen*.—None observed.

*Anthers*.—Size: 2 mm in length. Color: Yellow Group 11A. Quantity: 45 on average.

*Filaments*.—Color: Yellow Group 1A. Length: 6 mm.

*Pistils*.—Length: 7 mm. Quantity: 60 on average.

*Stigmas*.—Color: Yellow-White Group 158A.

*Styles*.—Color: Red Group 39B.

*Location of stigmas*.—Superior in location relative to the length of the filaments and the height of the anthers.

*Hips*.—None Observed.

PLANT

Plant growth: Upright, bushy. Plants are 60 cm in height, and 60 cm wide.

Stems:

*Color*.—Juvenile growth: Yellow-Green Group 144A. Mature growth: Yellow-Green Group 144A.

*Length*.—On average, canes are 50 cm from the base of the plant to the flowering portion.

*Diameter*.—4 to 5 mm.

*Internodes*.—On mature canes, there is an average distance of 40 mm between nodes.

*Surface texture*.—Young wood: Smooth. Older wood: Smooth.

Long prickles:

*Incidence*.—5 prickles per 10 cm of stem.

*Size*.—Average length of prickles on mature stems is 6 mm.

*Shape*.—Upper portion is linear. Lower portion is concave.

*Color*.—Juvenile prickles: Yellow-Green Group 144C with intonations of Greyed-Red Group 181B. Mature prickles: Yellow-Green Group 144C.

Plant foliage:

*Compound leaf*.—130 mm (l)×90 (w).

*Quantity*.—X leaves per 10 cm of stem on average.

*Leaf bearing angle to the stem*.—90 degrees.

*Color of juvenile foliage*.—Upper side: Yellow-Green Group 144A. Lower side: Yellow-Green Group 146C. Anthocyanin throughout the color of Greyed-Orange Group 174A.

*Color of mature foliage*.—Upper side: Yellow-Green Group 147A. Lower side: Yellow-Green Group 147B.

Plant leaves and leaflets:

*Stipules*.—Size: 20 mm in length. Width is about 10 mm. Quantity: 2 per compound leaf. Shape: Linear, slightly broad based with outward extending apices apecies. Margins: Finely serrated with few stipitate glands. Color: Yellow-Green Group 144A.

*Petiole*.—Length: 25 mm. Diameter: 2 mm.

*Upper surface*.—Color: Yellow-Green Group 144A.

*Lower surface*.—Color: Yellow-Green Group 144B. Observations: Few small prickles observed.

*Rachis*.—Length: 40 mm. Upper surface: Color: Yellow-Green Group 144A.

*Lower surface*.—Color: Yellow-Green Group 144B. Observations: Few small prickles observed.

*Leaflet*.—Quantity: Normal number of leaflets per leaf leaves in the middle of the stem is 5 leaflets. Margins: Serrated. Size: Average size of the terminal leaflet on normal leaves is 50 mm in length by 32 mm wide. Shape: Generally elliptical. Base: Rounded. Apex: Mucronate. Texture: Smooth. Thickness: Average. Arrangement: Odd pinnate. Venation: Reticulate. Glossiness: Not glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the floribunda rose class named 'Poulnap001', substantially as illustrated and described herein, due to its abundant pink flowers, disease resistance, and extended period of bloom.

* * * * *

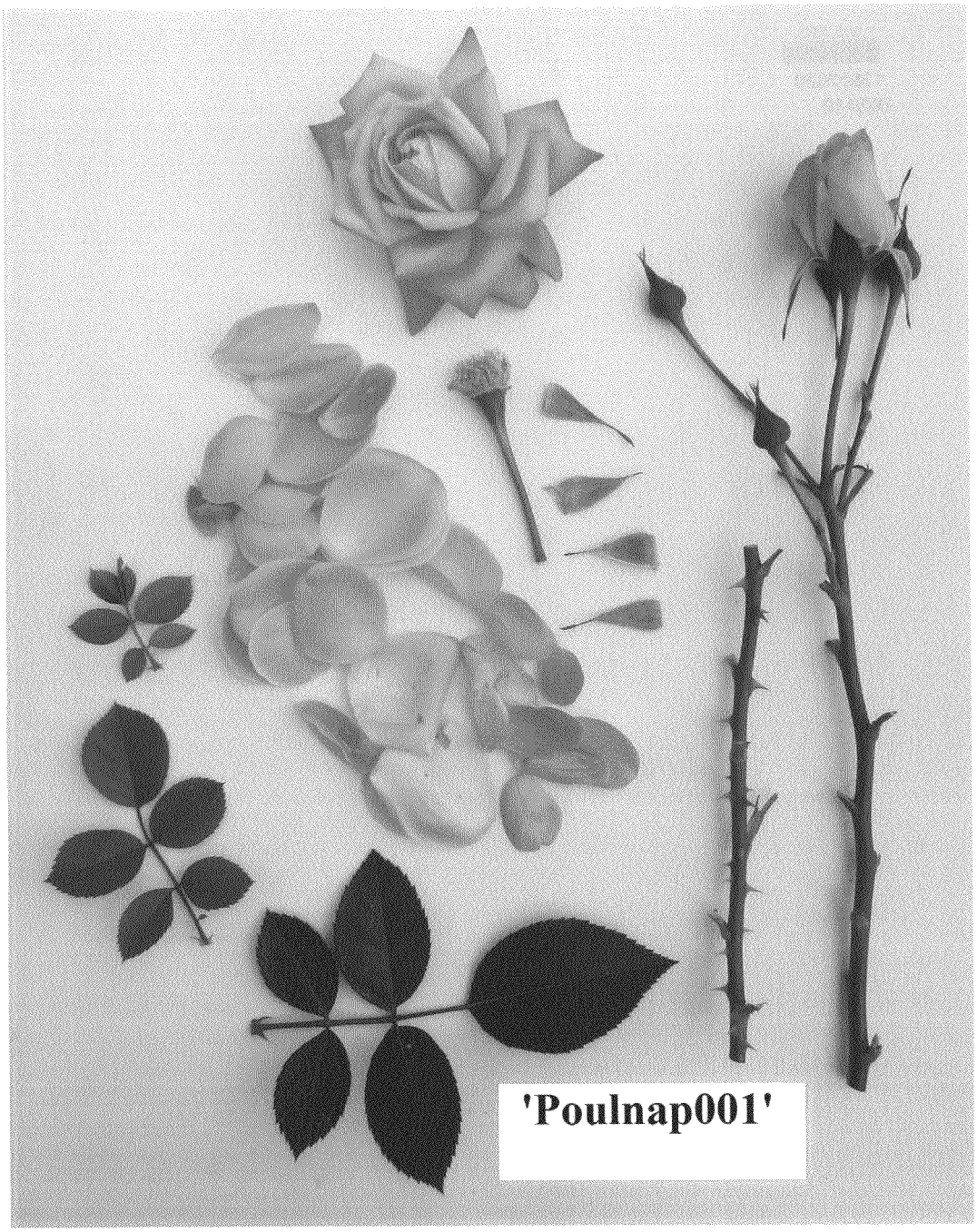
'Poulnap001'